United States Patent
McCutcheon et al.

(10) Patent No.: US 9,560,994 B2
(45) Date of Patent: Feb. 7, 2017

(54) PULSE OXIMETER WITH ADAPTIVE POWER CONSERVATION

(75) Inventors: Ian McCutcheon, Danville, CA (US); Scott Amundson, Oakland, CA (US); Ethan Petersen, Oakland, CA (US)

(73) Assignee: COVIDIEN LP, Mansfield, MA (US)

( * ) Notice: Subject to any disclaimer, the term of this patent is extended or adjusted under 35 U.S.C. 154(b) by 1002 days.

(21) Appl. No.: 12/409,715

(22) Filed: Mar. 24, 2009

(65) Prior Publication Data

US 2009/0247849 A1    Oct. 1, 2009

Related U.S. Application Data

(60) Provisional application No. 61/039,593, filed on Mar. 26, 2008.

(51) Int. Cl.
*A61B 5/1455*    (2006.01)
(52) U.S. Cl.
CPC .... *A61B 5/14551* (2013.01); *A61B 2560/0209* (2013.01)
(58) Field of Classification Search
CPC .................... A61B 2560/0209; A61B 5/14551
USPC ......... 600/323, 300, 310, 322, 509; 700/245
See application file for complete search history.

(56) References Cited

U.S. PATENT DOCUMENTS

| | | | |
|---|---|---|---|
| 4,942,877 A | 7/1990 | Sakai et al. | |
| 5,025,791 A * | 6/1991 | Niwa | A61B 5/14552 600/324 |
| 5,348,004 A | 9/1994 | Hollub | |
| 5,351,685 A | 10/1994 | Potratz | |
| 5,360,008 A | 11/1994 | Campbell, Jr. | |
| 5,368,026 A * | 11/1994 | Swedlow et al. | 600/323 |
| 5,408,314 A | 4/1995 | Perry et al. | |

(Continued)

FOREIGN PATENT DOCUMENTS

| | | |
|---|---|---|
| CN | 1642472 A | 7/2005 |
| EP | 734223 | 5/1998 |

(Continued)

OTHER PUBLICATIONS

Allen, J., "Photoplethysmography and its Application in Clinical Physiological Measurement," Physiol. Meas., vol. 28, Mar. 2007, pp. R1-R39.

(Continued)

*Primary Examiner* — Adam J Eiseman
*Assistant Examiner* — Patrick Fernandes

(57) ABSTRACT

Embodiments disclosed herein may include systems and methods for reducing power consumption of a pulse oximeter. The disclosure describes method for measuring oxygen saturation of a patient's blood with a pulse oximeter that switches between a high power mode of operation and one or more low power modes of operation based at least in part upon the data obtained from the patient or otherwise generated by the pulse oximeter. In one embodiment, the disclosure describes a operating a pulse oximeter in a high power mode, the pulse oximeter using a sensor to generate data indicative of the oxygen saturation of the patient's blood at a first resolution and switching the pulse oximeter to a low power mode upon detection of data indicative of a non-critical situation. The low power mode may be selected from a set of available low power modes based at least in part upon the data generated by the pulse oximeter.

18 Claims, 9 Drawing Sheets

(56) References Cited

U.S. PATENT DOCUMENTS

| | | |
|---|---|---|
| 5,457,790 A | 10/1995 | Iwamura et al. |
| 5,490,523 A | 2/1996 | Isaacson et al. |
| 5,533,507 A | 7/1996 | Potratz |
| 5,560,355 A | 10/1996 | Merchant et al. |
| 5,575,284 A | 11/1996 | Athan et al. |
| 5,577,500 A | 11/1996 | Potratz |
| 5,590,652 A | 1/1997 | Inai |
| 5,602,510 A | 2/1997 | Bayruns et al. |
| 5,645,068 A | 7/1997 | Mezack et al. |
| 5,657,215 A | 8/1997 | Faulk |
| 5,677,642 A | 10/1997 | Rehm et al. |
| 5,746,697 A * | 5/1998 | Swedlow et al. ............. 600/323 |
| 5,778,882 A | 7/1998 | Raymond et al. |
| 5,792,052 A | 8/1998 | Isaacson et al. |
| 5,803,910 A | 9/1998 | Potratz |
| 5,865,736 A | 2/1999 | Baker, Jr. et al. |
| 5,924,979 A | 7/1999 | Swedlow et al. |
| 5,990,948 A | 11/1999 | Sugiki |
| 6,005,658 A | 12/1999 | Kaluza et al. |
| 6,011,985 A | 1/2000 | Athan et al. |
| 6,141,169 A | 10/2000 | Pietruszynski et al. |
| 6,147,618 A | 11/2000 | Halleck et al. |
| 6,167,303 A | 12/2000 | Thompson |
| 6,185,454 B1 | 2/2001 | Thompson |
| 6,226,539 B1 | 5/2001 | Potratz et al. |
| 6,229,856 B1 | 5/2001 | Diab et al. |
| 6,236,888 B1 | 5/2001 | Thompson |
| 6,263,222 B1 | 7/2001 | Diab et al. |
| 6,324,426 B1 | 11/2001 | Thompson |
| 6,351,658 B1 | 2/2002 | Middleman et al. |
| 6,356,774 B1 | 3/2002 | Bernstein et al. |
| 6,377,185 B1 | 4/2002 | Halleck et al. |
| 6,381,479 B1 | 4/2002 | Norris |
| 6,397,092 B1 | 5/2002 | Norris et al. |
| 6,414,318 B1 | 7/2002 | Uber, III et al. |
| 6,434,425 B1 | 8/2002 | Thompson |
| 6,496,711 B1 | 12/2002 | Athan et al. |
| 6,496,729 B2 | 12/2002 | Thompson |
| 6,515,273 B2 | 2/2003 | Al-Ali |
| 6,629,638 B1 | 10/2003 | Sanchez |
| 6,643,530 B2 | 11/2003 | Diab et al. |
| 6,697,655 B2 | 2/2004 | Sueppel et al. |
| 6,697,658 B2 | 2/2004 | Al-Ali |
| 6,697,665 B1 | 2/2004 | Rava et al. |
| 6,711,426 B2 | 3/2004 | Benaron |
| 6,731,967 B1 | 5/2004 | Turcott |
| 6,734,802 B2 | 5/2004 | Halleck et al. |
| 6,745,060 B2 | 6/2004 | Diab et al. |
| 6,754,516 B2 | 6/2004 | Mannheimer |
| 6,760,608 B2 | 7/2004 | Lynn |
| 6,778,923 B2 | 8/2004 | Norris et al. |
| 6,863,652 B2 | 3/2005 | Huang et al. |
| 6,912,413 B2 * | 6/2005 | Rantala et al. ............... 600/322 |
| 7,003,338 B2 | 2/2006 | Weber et al. |
| 7,015,451 B2 | 3/2006 | Dalke et al. |
| 7,027,849 B2 | 4/2006 | Al-Ali |
| 7,072,702 B2 | 7/2006 | Edgar et al. |
| 7,123,950 B2 | 10/2006 | Mannheimer |
| 7,162,288 B2 | 1/2007 | Nordstrom et al. |
| 7,215,987 B1 | 5/2007 | Sterling et al. |
| 7,218,966 B2 | 5/2007 | Haefner |
| 7,246,620 B2 | 7/2007 | Conroy |
| 7,263,395 B2 | 8/2007 | Chan et al. |
| 7,295,866 B2 | 11/2007 | Al-Ali |
| 7,302,284 B2 | 11/2007 | Baker et al. |
| 7,315,753 B2 | 1/2008 | Baker et al. |
| 7,333,541 B2 | 2/2008 | Min et al. |
| 7,355,539 B2 | 4/2008 | Petersen et al. |
| 7,382,247 B2 | 6/2008 | Welch et al. |
| 7,425,201 B2 | 9/2008 | Euliano et al. |
| 7,438,683 B2 | 10/2008 | Al-Ali et al. |
| 7,486,386 B1 | 2/2009 | Holcombe et al. |
| 7,499,740 B2 | 3/2009 | Nordstrom et al. |
| 7,541,790 B2 | 6/2009 | Schopfer et al. |
| 7,630,078 B1 | 12/2009 | Nabutovsky et al. |
| 7,831,011 B2 | 11/2010 | Ayala et al. |
| 7,841,985 B2 | 11/2010 | Hicks |
| 7,843,978 B2 | 11/2010 | Souhaite et al. |
| 7,889,069 B2 | 2/2011 | Fifolt et al. |
| 7,996,187 B2 | 8/2011 | Nanikashvili et al. |
| 8,046,041 B2 | 10/2011 | Diab et al. |
| 8,078,248 B2 | 12/2011 | Lee et al. |
| 8,116,837 B2 | 2/2012 | Huang |
| 8,145,287 B2 | 3/2012 | Diab et al. |
| 8,150,487 B2 | 4/2012 | Diab et al. |
| 8,185,180 B2 | 5/2012 | Diab et al. |
| 2002/0103423 A1 | 8/2002 | Chin et al. |
| 2003/0028085 A1 | 2/2003 | Al-Ali |
| 2004/0002637 A1 * | 1/2004 | Huang ............... A61B 5/14551 600/300 |
| 2004/0054269 A1 | 3/2004 | Rantala et al. |
| 2004/0116969 A1 | 6/2004 | Owen et al. |
| 2004/0181133 A1 | 9/2004 | Al-Ali |
| 2004/0225225 A1 | 11/2004 | Naumov et al. |
| 2005/0070775 A1 | 3/2005 | Chin et al. |
| 2005/0070776 A1 | 3/2005 | Mannheimer et al. |
| 2005/0084202 A1 | 4/2005 | Smith et al. |
| 2005/0187446 A1 | 8/2005 | Nordstrom et al. |
| 2005/0209517 A1 | 9/2005 | Diab et al. |
| 2005/0234317 A1 | 10/2005 | Kiani |
| 2005/0250998 A1 | 11/2005 | Huiku |
| 2005/0256386 A1 | 11/2005 | Chan et al. |
| 2006/0081259 A1 | 4/2006 | Bruggeman et al. |
| 2006/0092029 A1 | 5/2006 | Browne et al. |
| 2006/0149144 A1 | 7/2006 | Lynn et al. |
| 2006/0173257 A1 | 8/2006 | Nagai et al. |
| 2006/0178588 A1 | 8/2006 | Brody |
| 2006/0217615 A1 | 9/2006 | Huiku et al. |
| 2006/0224059 A1 | 10/2006 | Swedlow et al. |
| 2006/0235324 A1 | 10/2006 | Lynn |
| 2006/0241506 A1 | 10/2006 | Melker et al. |
| 2006/0258921 A1 | 11/2006 | Addison et al. |
| 2007/0004977 A1 | 1/2007 | Norris |
| 2007/0027375 A1 | 2/2007 | Melker et al. |
| 2007/0032714 A1 | 2/2007 | Mannheimer |
| 2007/0038049 A1 * | 2/2007 | Huang .................... 600/323 |
| 2007/0043275 A1 | 2/2007 | Manheimer et al. |
| 2007/0055163 A1 | 3/2007 | Asada et al. |
| 2007/0106136 A1 | 5/2007 | Sterling et al. |
| 2007/0149860 A1 | 6/2007 | Lynn et al. |
| 2007/0191697 A1 | 8/2007 | Lynn et al. |
| 2007/0208236 A1 | 9/2007 | Hicks |
| 2007/0208240 A1 | 9/2007 | Nordstrom et al. |
| 2007/0221225 A1 | 9/2007 | Kutt et al. |
| 2007/0225581 A1 | 9/2007 | Diab et al. |
| 2007/0232951 A1 | 10/2007 | Euliano et al. |
| 2007/0282178 A1 | 12/2007 | Scholler et al. |
| 2007/0282183 A1 | 12/2007 | Scholler et al. |
| 2008/0045823 A1 | 2/2008 | Diab et al. |
| 2008/0064936 A1 | 3/2008 | Al-Ali |
| 2008/0067132 A1 | 3/2008 | Ross et al. |
| 2008/0081974 A1 | 4/2008 | Pav |
| 2008/0086440 A1 | 4/2008 | Hoey et al. |
| 2008/0097176 A1 | 4/2008 | Music et al. |
| 2008/0097177 A1 | 4/2008 | Music et al. |
| 2008/0108887 A1 | 5/2008 | Higgins |
| 2008/0132770 A1 | 6/2008 | Ayers et al. |
| 2008/0139953 A1 * | 6/2008 | Baker et al. .................. 600/509 |
| 2008/0161663 A1 | 7/2008 | Lee et al. |
| 2008/0190430 A1 | 8/2008 | Melker et al. |
| 2008/0200785 A1 | 8/2008 | Fortin |
| 2008/0208273 A1 | 8/2008 | Owen et al. |
| 2008/0228052 A1 | 9/2008 | Al-Ali |
| 2008/0278336 A1 | 11/2008 | Ortega et al. |
| 2008/0287756 A1 | 11/2008 | Lynn |
| 2008/0287757 A1 | 11/2008 | Berson et al. |
| 2008/0319290 A1 | 12/2008 | Mao et al. |
| 2009/0247846 A1 | 10/2009 | Rantala |
| 2009/0247849 A1 | 10/2009 | McCutcheon et al. |
| 2009/0259116 A1 | 10/2009 | Wasserman et al. |
| 2009/0270703 A1 | 10/2009 | Diab et al. |
| 2010/0016691 A1 | 1/2010 | Watson et al. |
| 2010/0056887 A1 | 3/2010 | Kimura et al. |
| 2010/0113909 A1 | 5/2010 | Batchelder et al. |

(56) References Cited

U.S. PATENT DOCUMENTS

| | | |
|---|---|---|
| 2010/0128838 A1 | 5/2010 | Ayala et al. |
| 2010/0179538 A1 | 7/2010 | Podhajsky |
| 2010/0234718 A1 | 9/2010 | Sampath et al. |
| 2010/0317937 A1 | 12/2010 | Kuhn et al. |
| 2011/0004081 A1 | 1/2011 | Addison et al. |
| 2011/0028854 A1 | 2/2011 | Addison et al. |
| 2011/0071406 A1 | 3/2011 | Addison et al. |
| 2012/0004519 A1 | 1/2012 | Nazarian et al. |
| 2012/0035485 A1 | 2/2012 | Owen et al. |
| 2012/0116193 A1 | 5/2012 | Huang |
| 2012/0184830 A1 | 7/2012 | Balberg et al. |
| 2012/0232354 A1 | 9/2012 | Ecker et al. |

FOREIGN PATENT DOCUMENTS

| | | |
|---|---|---|
| EP | 734221 | 7/1998 |
| EP | 1332713 | 8/2003 |
| EP | 1469773 | 10/2004 |
| JP | 2237544 | 9/1990 |
| JP | 3939782 | 7/2007 |
| WO | WO9516388 | 6/1995 |
| WO | WO9851212 A1 | 11/1998 |
| WO | WO0016839 | 3/2000 |
| WO | WO03063697 | 8/2003 |
| WO | 2006080856 | 8/2006 |
| WO | 2006083180 | 8/2006 |
| WO | WO2008039187 A1 | 4/2008 |
| WO | WO2008039195 | 4/2008 |
| WO | WO2008073584 | 6/2008 |

OTHER PUBLICATIONS

Murray, W. B., and Foster, P. A., "The Peripheral Pulse Wave: Information Overlooked," J. Clin. Monit., vol. 12, Sep. 1996, pp. 365-377.

Shelley, K. H., "Photoplethysmography: Beyond the Calculation of Arterial Oxygen Saturation and Heart Rate," Anesth. Analg., vol. 105, Dec. 2007, pp. S31-S36.

\* cited by examiner

PULSE OXIMETER WITH ADAPTIVE POWER CONSERVATION

RELATED APPLICATIONS

This application claims priority to U.S. Provisional Application No. 61/039,593, filed Mar. 26, 2008, and is incorporated herein by reference in its entirety.

BACKGROUND

In medicine, a plethysmograph is an instrument that measures variations in the size of an organ or body part on the basis of the amount of blood passing through or present in the part. An oximeter is a type of plethysmograph that determines the oxygen saturation of the blood. One common type of oximeter is a pulse oximeter.

A pulse oximeter is a medical device that indirectly measures the oxygen saturation of a patient's blood (as opposed to measuring oxygen saturation directly through a blood sample) and changes in blood volume in the skin.

A pulse oximeter may include a light sensor that is placed at a site on a patient, usually a fingertip, toe, forehead or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

SUMMARY

This disclosure describes systems and methods for reducing the power consumption of a pulse oximeter. As discussed in greater detail below, the disclosure describes methods for measuring oxygen saturation of a patient's blood with a pulse oximeter that switches between a high power mode of operation and one or more low power modes of operation based at least in part upon the data obtained from the patient or otherwise generated by the pulse oximeter. In an embodiment, the disclosure describes operating a pulse oximeter in a high power mode, the pulse oximeter using a sensor to generate data indicative of the oxygen saturation of the patient's blood at a first resolution and switching the pulse oximeter to a low power mode upon detection of data indicative of a non-critical situation. The low power mode may be selected from a set of available low power modes based at least in part upon the data generated by the pulse oximeter.

The disclosure further describes a method for measuring oxygen saturation of a patients blood which includes operating a pulse oximeter in a high power mode, in which the pulse oximeter uses a sensor to generate data indicative of the oxygen saturation of the patient's blood at a first resolution. The method then compares the data generated by the pulse oximeter to one or more predefined data profiles indicative of a non-critical situation. Upon detection that the data matches at least one predefined data profile, the method selects a low power mode based on the predefined data profile matched by the data. The pulse oximeter is then switched to the selected low power mode.

Among other things, the disclosure also describes a pulse oximeter comprising a high power mode of operation and a power conservation engine that, upon determination that the data generated by the pulse oximeter matches at least one of a set of data profiles, switches the pulse oximeter into one of a set of low power modes of operation based on the data profile matching the data generated by the pulse oximeter.

The set of predefined data profiles used by the pulse oximeter may include a first data profile associated with a moving patient, a second data profile associated with a patient with a stable pulse and stable oxygen saturation, a third data profile associated with a pulse oximeter that is not properly installed on a patient; a fourth data profile associated with a pulse oximeter that is used in conjunction with an electrocardiograph monitoring the patient, and a fifth data profile associated with a user-selected power savings mode. In addition, the set of low power modes may include a first low power mode that reduces a number of samples taken within a period of time, a second low power mode that reduces a signal-to-noise ratio of data generated by the pulse oximeter, a third low power mode that uses a different data processing algorithm than that used in the high power mode, a fourth low power mode that causes the pulse oximeter to obtain data from only one of a plurality of light sources in the sensor, and a fifth low power mode that reduces a sampling resolution of the data generated by the pulse oximeter.

These and various other features as well as advantages which characterize the disclosed systems and methods will be apparent from a reading of the following detailed description and a review of the associated drawings. Additional features of the systems and methods described herein are set forth in the description which follows, and in part will be apparent from the description, or may be learned by practice of the technology. The benefits and features will be realized and attained by the structure particularly pointed out in the written description and claims hereof as well as the appended drawings.

It is to be understood that both the foregoing general description and the following detailed description are exemplary and explanatory and are intended to provide further explanation of the disclosed technology as claimed.

BRIEF DESCRIPTION OF THE DRAWINGS

The following drawing figures, which form a part of this application, are illustrative of disclosed technology and are not meant to limit the scope of the description in any manner, which scope shall be based on the claims appended hereto.

DETAILED DESCRIPTION

This disclosure generally describes systems and methods for reducing the power consumption of a pulse oximeter. Pulse oximetry is often performed over long periods of time. However, as more and more pieces of medical equipment are powered by batteries, the power consumption of a traditional pulse oximeter can require an inconveniently large battery supply. The techniques described herein allow for a pulse oximeter to select and operate in different power modes depending on the situation.

Although the techniques for reducing power consumption introduced above and discussed in detail below may be implemented for a variety of medical devices, the present disclosure will discuss the implementation of these techniques in a pulse oximetry system. The reader will understand that the technology described in the context of a pulse oximetry system could be adapted for use with other systems such as a combined medical monitoring system that utilizes pulse oximetry data.

Figure 1:
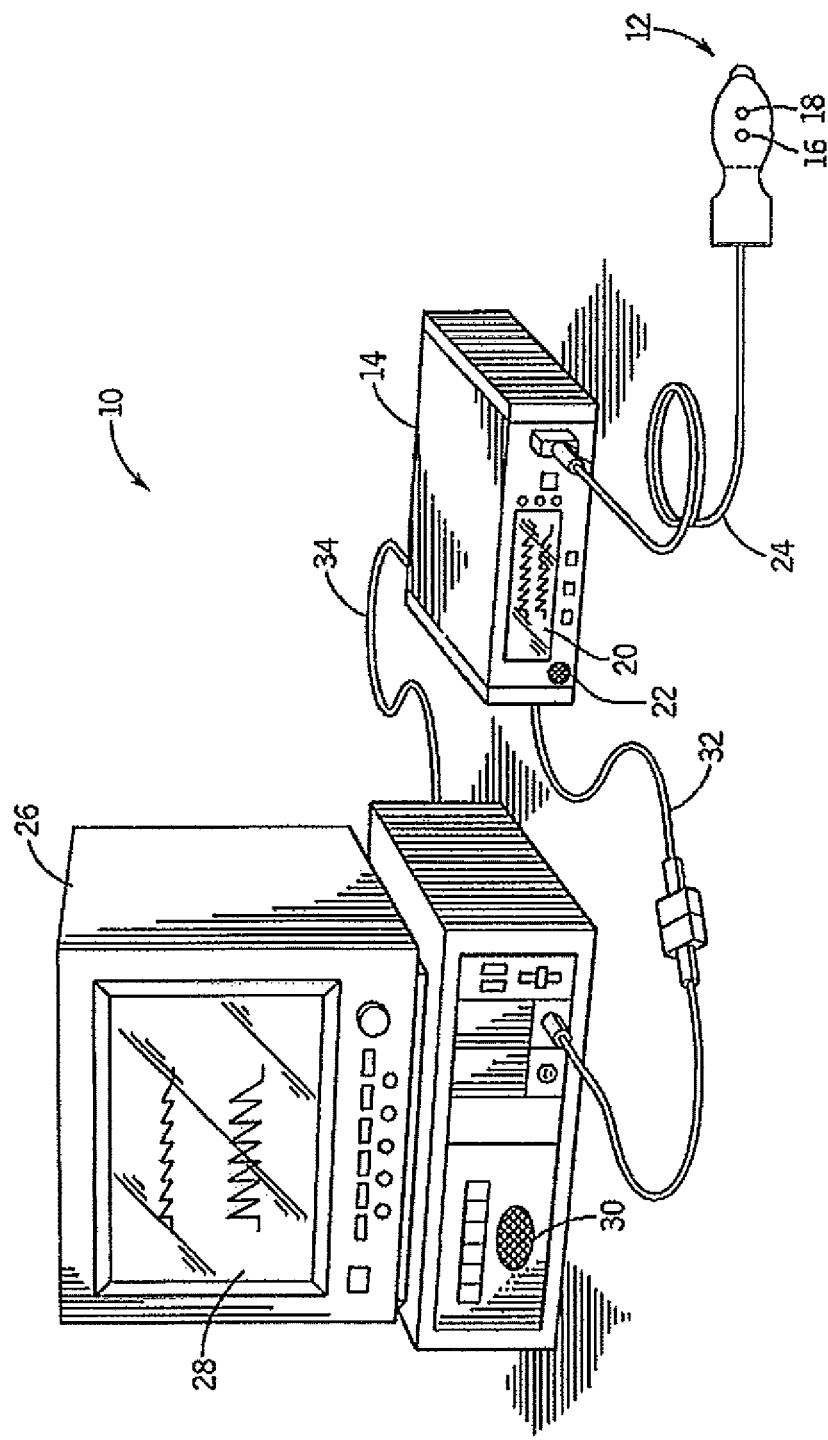
FIG. 1 is a perspective view of a pulse oximetry system, according to an embodiment.

FIG. 1 is a perspective view of an embodiment of a pulse oximetry system 10. The system 10 includes a sensor 12 and a pulse oximetry monitor 14. The sensor 12 includes an emitter 16 for emitting light at one or more wavelengths into a patient's tissue. A detector 18 is also provided in the sensor 12 for detecting the light originally from the emitter 16 that emanates from the patient's tissue after passing through the tissue. The emitter 16 and detector 18 may be on opposite sides of a digit such as a finger or toe, in which case the light that is emanating from the tissue has passed completely through the digit. In an alternative embodiment, the emitter 16 and detector 18 may be arranged so that light from the emitter 16 penetrates the tissue and is reflected by the tissue into the detector 18, such as a sensor designed to obtain pulse oximetry data from a patient's forehead.

The sensor may be connected to and draw its power from the monitor 14 as shown. Alternatively, the sensor may be wirelessly connected to the monitor 14 and include its own battery or similar power supply (not shown). In terms of operating in different power consumption modes, the sensor 12 may be adapted to operate in multiple modes each consuming a different amount of power. In all embodiment, each different mode may correspond to using a different mix of sensor equipment including light sources and/or a different data sampling regime as described below. For example, in the embodiment illustrated in FIG. 1, in a high power consumption mode (referred to as the "high power mode"), the sensor 12 may take light measurements using both light sources in the emitter 16 while in a low power mode only one light source may be used. Such a low power mode may also selectively de-energize components in the detector 18 for use with the de-energized light source.

The monitor 14 may be configured to calculate physiological parameters based on data received from the sensor 12 relating to light emission and detection. Further, the monitor 14 includes a display 20 configured to display the physiological parameters, other information about the system, and/or alarm indications. In the embodiment shown, the monitor 14 also includes a speaker 22 to provide an audible alarm in the event that the patient's physiological parameters are not within a normal range, as defined based on patient characteristics. The sensor 12 is communicatively coupled to the monitor 14 via a cable 24. However, in other embodiments a wireless transmission device (not shown) or the like may be utilized instead of or in addition to the cable 24.

In the illustrated embodiment, the pulse oximetry system 10 also includes a multi-parameter patient monitor 26. The multi-parameter patient monitor 26 may be configured to calculate physiological parameters and to provide a central display 28 for information from the monitor 14 and from other medical monitoring devices or systems (not shown). For example, the multiparameter patient monitor 26 may be configured to display a patient's oxygen saturation reading generated by the pulse oximetry monitor 14 (referred to as an "SpO$_2$" reading), pulse rate information from the monitor 14 and blood pressure from a blood pressure monitor (not shown) on the display 28. Additionally, the multi-parameter patient monitor 26 may emit a visible or audible alarm via the display 28 or a speaker 30, respectively, if the patient's physiological characteristics are found to be outside of the normal range. The monitor 14 may be communicatively coupled to the multi-parameter patient monitor 26 via a cable 32 or 34 coupled to a sensor input port or a digital communications port, respectively. In addition, the monitor 14 and/or the multi-parameter patient monitor 26 may be connected to a network to enable the sharing of information with servers or other workstations (not shown). The monitor 14 may be powered by a battery (not shown) or by a conventional power source such as a wall outlet.

In an embodiment, the monitor 14 may also be adapted to operate in a plurality of power consumption modes as described in greater detail below. The monitor 14 may select its mode of operation in real-time based on an analysis of the data obtained from the sensor 12, or in response to commands received from an operator.

Figure 2:
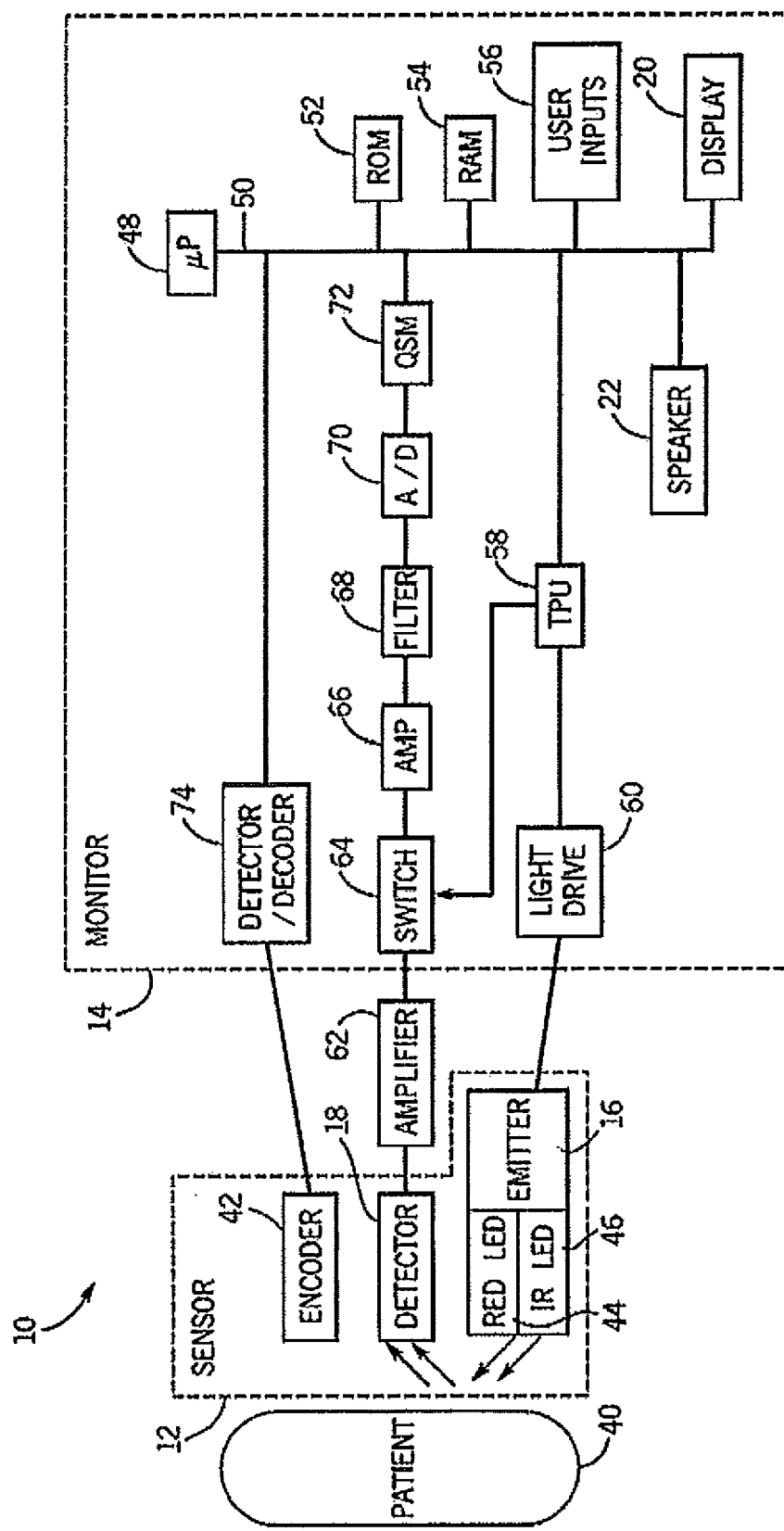
FIG. 2 is a block diagram of the embodiment of a pulse oximetry system of FIG. 1 coupled to a patient.

FIG. 2 is a block diagram of the exemplary pulse oximetry system 10 of FIG. 1 coupled to a patient 40 in accordance with present embodiments. Specifically, certain components of the sensor 12 and the monitor 14 are illustrated in FIG. 2. The sensor 12 includes the emitter 16, the detector 18, and an encoder 42. In the embodiment shown, the emitter 16 is configured to emit at least two wavelengths of light, e.g., RED and IR, into a patient's tissue 40. Hence, the emitter 16 may include a RED light emitting light source such as the RED light emitting diode (LED) 44 shown and an IR LED 46 for emitting light into the patient's tissue 40 at the wavelengths used to calculate the patient's physiological parameters. In certain embodiments, the RED wavelength may be between about 600 nm and about 700 nm, and the IR wavelength may be between about 800 nm and about 1000 nm. Depending on the current power consumption mode that the sensor 12 is operating in, one or more of the light sources may be de-energized to save power.

Alternative light sources may be used in other embodiments. For example, a single wide-spectrum light source may be used, and the detector 18 may be configured to detect light only at certain wavelengths. Alternatively, a third light source may be provided based on its ability to obtain an accurate signal when the starting oxygen saturation is known while consuming less power. In another example, the detector 18 may detect a wide spectrum of wavelengths of light, and the monitor 14 may process only those wavelengths which are of interest or which take the least power to detect.

It should be understood that, as used herein the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet or X-ray spectra, and that any suitable wavelength of light may be appropriate for use with the present techniques.

In an embodiment, the detector 18 may be configured to detect the intensity of light at the RED and IR wavelengths. In operation, light enters the detector 18 after passing through the patient's tissue 40. The detector 18 converts the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, the detector 18 sends the signal to the monitor 14, where physiological parameters may be calculated based on the absorption of the RED and IR wavelengths in the patient's tissue 40. An example of a device configured to perform such calculations is the Model N600x pulse oximeter available from Nellcor Puritan Bennett LLC.

The encoder 42 may contain information about the sensor 12, such as what type of sensor it is (e.g., whether the sensor is intended for placement on a forehead or digit) and the wavelengths of light emitted by the emitter 16. This information may be used by the monitor 14 to select appropriate algorithms, lookup tables and/or calibration coefficients stored in the monitor 14 for calculating the patient's physiological parameters.

In addition, the encoder 42 may contain information specific to the patient 40, such as, for example, the patient's age, weight and diagnosis. This information may allow the monitor 14 to determine patient-specific threshold ranges in which the patient's physiological parameter measurements should fall and to enable or disable additional physiological parameter algorithms. The encoder 42 may, for instance, be a coded resistor which stores values corresponding to the type of the sensor 12, the wavelengths of light emitted by the emitter 16, and/or the patient's characteristics. These coded values may be communicated to the monitor 14, which determines how to calculate the patient's physiological parameters and alarm threshold ranges. In another embodiment, the encoder 42 may include a memory on which one or more of the following information may be stored for communication to the monitor 14: the type of the sensor 12; the wavelengths of light emitted by the emitter 16; the proper calibration coefficients and/or algorithms to be used for calculating the patient's physiological parameters and/or alarm threshold values; the patient characteristics to be used for calculating the alarm threshold values; and the patient-specific threshold values to be used for monitoring the physiological parameters.

Signals from the detector 18 and the encoder 42 may be transmitted to the monitor 14. In the embodiment shown, the monitor 14 includes a general-purpose microprocessor 48 connected to an internal bus 50. The microprocessor 48 is adapted to execute software, which may include an operating system and one or more applications, as part of performing the functions described herein. Also connected to the bus 50 are a read-only memory (ROM) 52, a random access memory (RAM) 54, user inputs 56, the display 20, and the speaker 22.

The RAM 54 and ROM 52 are illustrated by way of example, and not limitation. Any computer-readable media may be used in the system for data storage. Computer-readable media are capable of storing information that can be interpreted by the microprocessor 48. This information may be data or may take the form of computer-executable instructions, such as software applications, that cause the microprocessor to perform certain functions and/or computer-implemented methods. Depending on the embodiment, such computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 provides timing control signals to a light drive circuitry 60 which controls when the emitter 1b6 is illuminated and multiplexed timing for the RED LED 44 and the IR LED 46. The TPU 58 also controls the gating-in of signals from detector 18 through an amplifier 62 and a switching circuit 64. These signals are sampled at the proper time, depending upon which light source is illuminated. The received signal from the detector 18 may be passed through an amplifier 66, a low pass filter 68, and an analog-to-digital converter 7b0. The digital data may then be stored in a queued serial module (QSM) 72 (or buffer) for later downloading to the RAM 54 as the QSM 72 fills up. In one embodiment, there may be multiple separate parallel paths having the amplifier 66, the filter 68, and the A/D converter 70 for multiple light wavelengths or spectra received.

The microprocessor 48 may determine the patient's physiological parameters, such as $SpO_2$ and pulse rate, using various algorithms and/or look-up tables based on the value of the received signals corresponding to the light received by the detector 18. Signals corresponding to information about the patient 40, and particularly about the intensity of light emanating from a patient's tissue over time, may be transmitted from the encoder 42 to a decoder 74. These signals may include, for example, encoded information relating to patient characteristics. The decoder 74 may translate these signals to enable the microprocessor to determine the thresholds based on algorithms or look-up tables stored in the ROM 52. The encoder 42 may also contain the patient-specific alarm thresholds, for example, if the alarm values are determined on a workstation separate from the monitor 14. The user inputs 56 may also be used to enter information about the patient, such as age, weight, height, diagnosis, medications, treatments, and so forth. In certain embodiments, the display 20 may exhibit a list of values which may generally apply to the patient, such as, for example, age ranges or medication families, which the user may select using the user inputs 56. The microprocessor 48 may then determine the proper thresholds using the user input data and algorithms stored in the ROM 52. The patient-specific thresholds may be stored on the RAM 54 for comparison to measured physiological characteristics.

The memory 52, 54 may also store information for use in selection of a power consumption mode based on the data generated by the sensor 12 and/or monitor 14. For example, in an embodiment one or more data profiles are stored which are used to determine when the data obtained from a patient or otherwise generated by the pulse oximeter indicates that the system should switch to a low power mode. A data profile may be an algorithm, look up table or other representation of data to which the generated data may be compared. As discussed below, if a match is detected the system may then switch to a low power mode of operation until some trigger causes the system to switch to another power consumption mode, e.g., back to a high power mode. Furthermore, the profiles may include an identification of which power consumption mode to use when a profile is matched by the data.

In an embodiment, the various power consumption modes may also be stored in memory 52, 54. For example, the memory 52, 54 may include a listing of specific actions to be performed or not to be performed or a list of components to be energized or de-energized while in a specific power mode. Alternatively, in a hardware embodiment the various power modes may be incorporated into the hardware or firmware of the system.

In an embodiment, the data profiles and corresponding power consumption modes may be provided with the pulse oximeter. Alternatively or in addition, one or more of the data profiles and corresponding power consumption modes may downloading into the pulse oximeter at a later time, allowing the pulse oximeter to be modified to operate in a low power mode as needed throughout the life of the oximeter.

In an embodiment, it is anticipated that a set of data profiles has been provided in which each data profile corresponds to a different non-critical situation. By non-critical situation, it is meant a situation in which the operators or manufacturer deem the extra accuracy, precision and response time of the high power mode is not beneficial due to other factors such as the status of the patient, quality of the data obtainable while in the high power mode or status of the equipment. Examples of different data profiles are described in greater detail below. Furthermore, each data profile may be associated with a different power mode in which each power mode results in reduced power consumption in comparison to the high power mode, while further being adapted to obtain at least an adequate measurement or output considering the circumstances.

Figure 3:
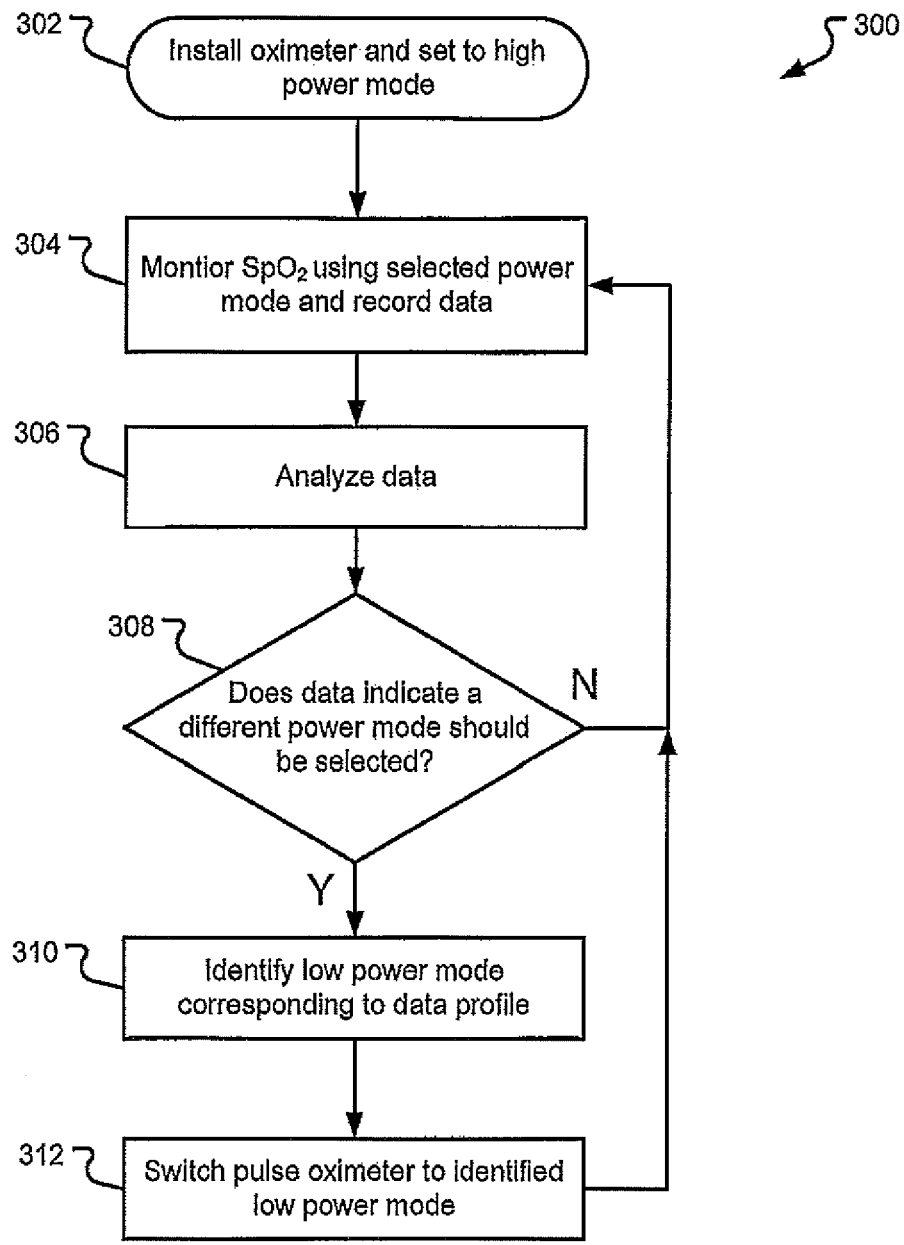
FIG. 3 illustrates an embodiment of a method for conserving power while measuring the oxygen saturation of a patient's blood.

FIG. 3 illustrates an embodiment of a method for conserving power while measuring the oxygen saturation of a patient's blood. The method 300 is directed to determining when different power consumption mode should be used by a pulse oximeter. This is fundamentally different from low power pulse oximeters, as well as pulse oximeters with simple "sleep" states, as the power consumption modes are selected based on the data observed by the pulse oximeter.

The method 300 starts with the installation of the pulse oximeter at a site on the patient in an installation operation 302. As discussed above, such a site (which may alternately be referred to as a location) may include a digit, the forehead or some other site from which a pulse oximeter can obtain an oxygen saturation measurement. The installation operation 302 includes attaching the pulse oximeter to the site and initiating the oxygen saturation measurement. As discussed above, this includes directing of light from a light source into tissue of a patient and measuring with a detector the light emanating from the tissue of the patient at the monitoring site.

The installation operation 302 is then followed by a period in which the pulse oximeter generates data and determines the oxygen saturation of the blood of the patient in an ongoing monitoring operation 304. In the monitoring operation 304, the pulse oximeter is operated in a high power mode and used to monitor the oxygen saturation of the patient's blood by monitoring the light detected emanating from the monitoring site. In an embodiment the high power mode of operation allows the pulse oximeter to obtain the most accurate and quickest oxygen saturation measurements. The monitoring may be continuous, periodic, of even occasional depending upon the medical needs at the time. However, the monitoring is ongoing and lasts for an extended period of time.

In an embodiment, during the monitoring operation 304, the oxygen saturation of the patient's blood is calculated based on the most recent data received from the sensor in order to provide a current measurement of the oxygen saturation. As is known in the art, the current oxygen saturation may be displayed in real time and analyzed based on patient characteristics. For example, the current measurements may be compared to thresholds if the measurements exceed a threshold range or amount various alarms may be triggered. The oxygen saturation measurements may be generated by a sophisticated algorithm and may utilize a significant amount of processor cycles and signal processing hardware (e.g., filters, amplifiers, high-resolution digital to analog converters, etc.).

During the monitoring operation 304, in addition to the monitoring of the current oxygen saturation and its subsequent display to the medical caregivers, the method 300 may also record at least some of the data received from the pulse oximeter for comparison to the power consumption data profiles. The data recorded may be filtered or unfiltered, analog or digital data or a combination of data depending upon the amount and type of data necessary for comparison to the data profiles. In addition, not all data received from the detector of the pulse oximeter may be stored, but rather only a subset a data may be stored as necessary to perform a later analysis to determine if a data profile is matched. Similarly, the amount of data recorded may also depend on the amount of data necessary to determine if a data profile is matched.

In the embodiment shown, while the oximeter is monitoring the patient the method 300 analyzes the data generated by the pulse oximeter to determine if it should switch to a low power mode in an analysis operation 306. In an embodiment, the analysis operation 306 may include comparing the data to the various data profiles. As described above, a data profile may be a series of data points, an algorithm or a characteristic of data that can be used to determine if the data generated by the oximeter matches some predetermined data sequence that is known to be indicative of a non-critical situation such as a stable patient or other situation in which the accuracy and response time of the high power mode is not necessary.

If the analysis operation 306 determines that the system should remain in the current power mode, the method returns to the monitoring operation 304. This is illustrated by the determination operation 308. In an embodiment, the determination operation 308 may determine that the oximeter should operate in a high power mode if the data does not match any data profiles associated with a low power mode, e.g., when the data generated by the pulse oximeter is determined not to match any of the data profiles. In an alternative embodiment, a data profile may in fact be provided for one or more high power modes and the determination operation 308 may determine that the data matches a high power data profile. Thus, in one or more embodiments, the determination operation 308 includes determining which power consumption mode the oximeter is currently operating in.

If, however, it is determined that the data matches one of the low power data profiles, the method 300 performs a identification operation 310 in which the low power mode that is associated with the data profile matched by the data is identified and, if necessary, retrieved from memory. For example, in an embodiment in which multiple data profiles are stored and two or more of the data profile correspond to different low power modes, the low power mode associated with the matched data profile is identified and retrieved, if necessary, from memory.

After the low power mode has been identified, the method 300 switches the operation of the pulse oximeter from the high power mode to the low power mode in a switch power mode operation 312. The control flow then returns to the monitoring mode 304 so that the oximeter operates in the low power mode. Depending on the low power mode identified in the identification operation 310, the type and amount of data generated by the pulse oximeter, including how it is analyzed, stored and displayed may vary. Examples of different low power modes are described in greater detail below.

In the embodiment shown, due to the flow of the embodiment shown the data generated while in low power mode is periodically analyzed to determine if the pulse oximeter should return to a high power mode. This is illustrated by the control flow returning to the analysis operation 306. This allows the data generated in low power mode to be analyzed and potentially be determined to match another data profile (and which may include a data profile or lack thereof associated with the high power mode), after which the method switches to the corresponding power mode. In an alternative embodiment (not shown), while in a low power mode the method may only monitor the data generated for an indication that the oximeter should be returned to a high power mode.

It should be noted that the window of time over which the data is analyzed in the analysis operation 306 may vary depending on the data profile being tested. Furthermore, the amount and type of data analyzed in the analysis operation 306 may be different depending on which data profile is being tested. The analysis operation 306 may include one or more different analyses of the recorded data. For example, in an embodiment, the analysis includes identifying changes (or lack thereof) in one or more characteristics such as the $SpO_2$ measurement, the pulse amplitude of one or more of the signals from the sensor, the signal strength of one or more of the signals from the sensor, and the pulse shape as indicated by the signals from the sensor.

An analysis of the $SpO_2$ measurement may include comparing the measurements taken at the beginning of the time period being analyzed and those taken at the end. Alternatively, the analysis could include a mathematical analysis of how the $SpO_2$ measurements have changed over time. The results of the comparison or mathematical analysis may then be compared to a benchmark or threshold in order to determine if the $SpO_2$ measurements taken over time have remained stable.

An analysis of the pulse amplitude may include comparing the pulse amplitudes observed at the beginning of the time period being analyzed and those taken at the end. Alternatively, the analysis could include a mathematical analysis of how the pulse amplitudes have changed over time. In addition, the pulse amplitudes of the RED and IR signals could be independently analyzed and then compared to each other. The results may then be compared to a benchmark or threshold in order to determine if the pulse amplitudes have changed over time to the extent that they indicate that the patient is stable or that an otherwise non-critical situation is occurring.

An analysis of the signal strength may include comparing the signal strengths observed at the beginning of the time period being analyzed and those taken at the end. Alternatively, the analysis could include a mathematical analysis of how the signal strength has changed over time. In addition, the signal strength of the RED and IR signals could be independently analyzed and then compared to each other. The results may then be compared to a benchmark or threshold in order to determine if the pulse amplitudes have changed over time to the extent that they indicate that a non-critical situation is occurring.

An analysis of the pulse shape may include comparing the pulse shapes observed at the beginning of the time period being analyzed and those taken at the end. Alternatively, the analysis could include a mathematical analysis of how the pulse shapes have changed over time. In addition, the pulse shapes of the RED and IR signals could be independently analyzed and then compared to each other. The results may then be compared to a benchmark or threshold in order to determine if the pulse shapes have changed over time to the extent that they indicate that the a non-critical situation is occurring. Alternatively, the pulse shapes may be compared to a representative pulse shape that is indicative of a non-critical situation.

As mentioned above, in alternative embodiments filtered data, unfiltered data or both filtered and unfiltered data may be analyzed in the analysis operation 306. Unfiltered data may be useful in detecting characteristics that would be filtered out in the process of obtaining an accurate $SpO_2$ measurement. For example, in an embodiment the $2^{nd}$, $3^{rd}$ and $4^{th}$ harmonics in the data may be determined mathematically and the results compared to a predetermined threshold. Determination of such harmonics would be altered if filtered versus unfiltered data were used.

The thresholds or acceptable ranges used in the analysis operation 306 to determine if a site has degraded may be empirically determined by prior experiments on patients. In addition, different thresholds/ranges may be used depending on the characteristics of the patient and the needs and preferences of the caregiver.

Figure 4:
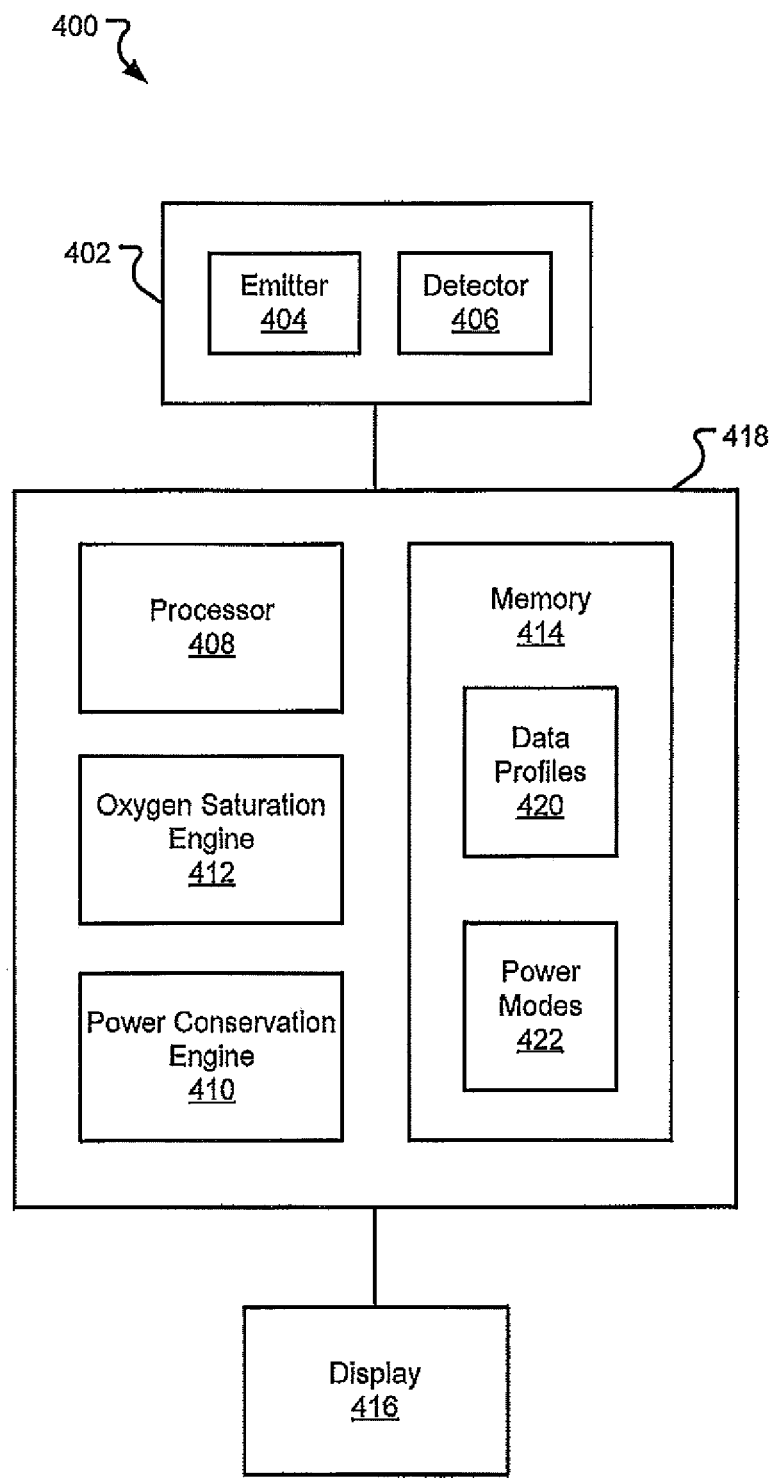
FIG. 4 is a block diagram illustrating some of the components of a pulse oximetry system with different power modes, according to an embodiment.

FIG. 4 is a block diagram illustrating some of the components of a pulse oximetry system with different power modes. In the embodiment shown, the system 400 includes a sensor 402 containing a light emitter 404 and a light detector 406; and, in a separate housing 418, a processor 408, a power conservation 410; an oxygen saturation engine 412; and a memory 414. A display 416 is also provided. The sensor 402 and its components operate as described previously with reference to FIG. 2.

The memory 414 may include RAM, flash memory or hard disk data storage devices. The memory stores data, which may be filtered or unfiltered data, received from the detector 406. The data may be decimated, compressed or otherwise modified prior to storing in the memory 414 in order to increase the time over which data may be retained.

The oxygen saturation engine 412 generates a current oxygen saturation measurement from the data generated by the sensor. In an embodiment, the oxygen saturation engine 412 is a dedicated hardware circuit that may include filters, firmware comprising lookup tables or other data, and its own processor (not shown) that allow it to generate the current oxygen saturation measurement. In an alternative embodiment, the oxygen saturation engine 412 may be implemented as a software application that is executed, in whole or in part, by the system processor 408. In yet another embodiment, functions described herein as being performed by the oxygen saturation engine 412 may be distributed among hardware, software and firmware throughout the system 400 and its other components.

In the embodiment shown, the memory 414 contains a set of data profiles 420 which define different data sequences or characteristics which, when they are detected by the power conservation engine 410, should cause the oximeter 418 to change to a different power consumption mode. In the embodiment shown, the different power consumption modes 422 are also stored in the memory 414. For example, in an embodiment, if any of the set of data profiles 4b20 is detected, the corresponding power mode 422 is identified and the oximeter 418 is switched to operate in that mode 422.

The power conservation engine 410 performs the analyses of the data generated by the oximeter 418 and, upon determination that the data generated by the oximeter 418 matches a data profile (e.g., the data indicates that there is a non-critical situation is occurring), handles the switching of the operational mode of the oximeter 418 to the identified power mode 4b22. This includes switching from a high power mode to a low power mode and vice versa.

The display 416 may be any device that is capable of generating a audible or visual notification. The display need not be integrated into the other components of the system 400 and could be a wireless device or even a monitor on a general purpose computing device (not shown) that receives email or other transmitted notifications from the oximeter 418. In an embodiment, the mode of operation of the system may not be communicated to the operator. Alternatively, the system 400 may indicate to an operator what mode the system is currently in and allow the operator to override a mode selected by the power conservation engine 410.

The power modes 422 may include a plurality of different low power modes that could be independently selected based on the matched data profile 420. For example, in an embodiment the memory may store a first low power mode that reduces a number of samples taken by the pulse oximeter within a period of time; a second low power mode that reduces a signal-to-noise ratio of data generated by detectors used by the pulse oximeter, such as by lowering the LED power thereby decreasing the intensity of light at the detector; a third low power mode that uses a different data processing algorithm than that used in the high power mode, such as a simple algorithm that is less accurate or precise than the algorithm used in the high power mode; a fourth low power mode that causes the pulse oximeter to obtain data from only one of a plurality of light sources in the sensor, e.g., from only the RED or IR LED and extrapolate the oxygen saturation measurements from the single measurement based on earlier measurements; and a fifth low power mode that reduces a sampling resolution of the data generated by the pulse oximeter. Other power modes are also possible and within the scope of this disclosure.

Figure 5:
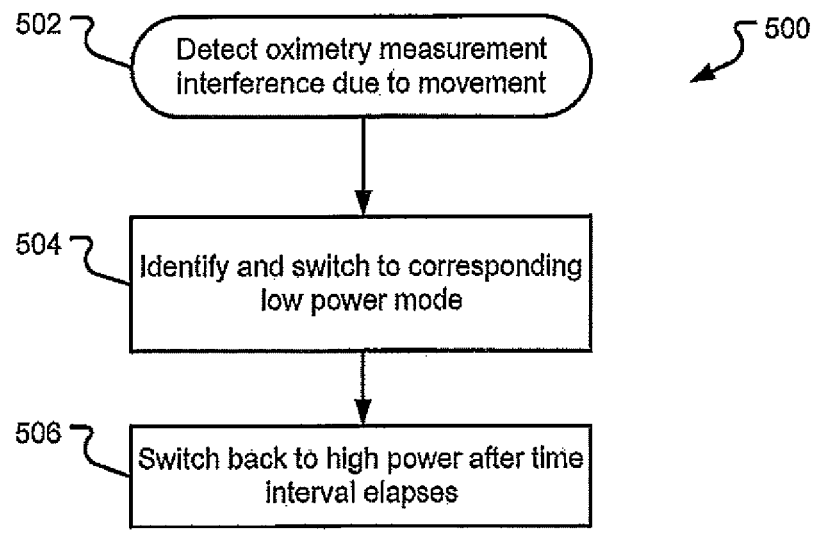
FIG. 5 illustrates an embodiment of a method for selecting a low power mode in response to determining that patient movement is interfering with pulse oximetry measurements.

FIG. 5 illustrates an embodiment of a method for selecting a low power mode in response to determining that patient movement is interfering with pulse oximetry measurements. In the embodiment shown, a data profile is provided that is indicative of the data received from a stable, non-critical patient that is moving the pulse oximeter. Movement of the pulse oximeter can cause interference with the pulse oximetry measurements and otherwise lead to poor readings. In an embodiment, it may not be desirable to use power while a patient is moving in order to obtain what is destined to be a poor reading anyway. Furthermore, patient movement may be considered indicative of a patient healthy enough to move.

In the method 500 illustrated in FIG. 5, a detection operation 502 determines from the data that patient is moving. This may be determined from the pulse oximetry data itself or from some other source such as a movement detector included in the sensor. In an embodiment, the data is compared to a data profile indicative of oximetry movement. Upon detection that movement is affecting the characteristics of the data generated by the pulse oximeter in the high power mode, a switching operation 504 is performed in which the pulse oximeter is switched to a low power mode corresponding to the movement data profile. The low power mode associated with movement may be a mode in which no measurements are taken or any one or more of the low power modes described above.

Furthermore, in the embodiment shown, the method 500 remains in the low power mode for a predetermined time interval and) after the time interval has elapsed, returns the pulse oximeter to the high power mode in high power mode operation 506.

Figure 6:
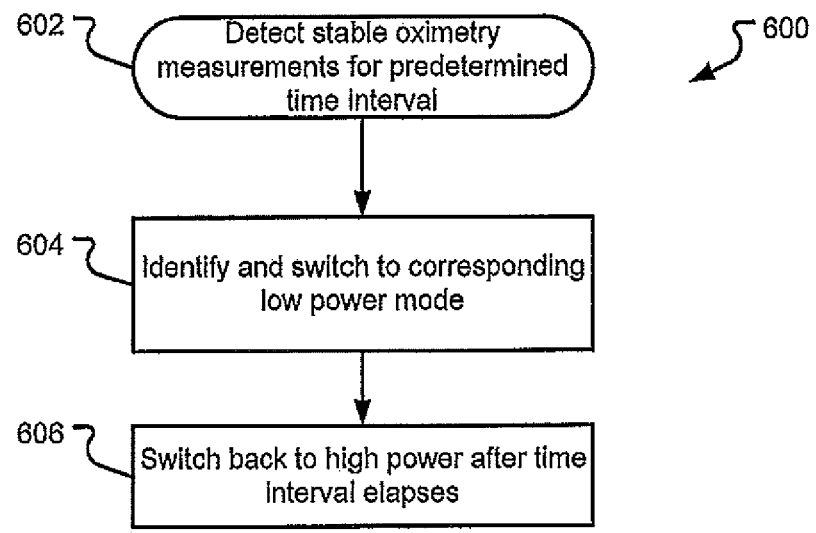
FIG. 6 illustrates an embodiment of a method for selecting a low power mode in response to stable pulse oximetry measurements.

FIG. 6 illustrates an embodiment of a method for selecting a low power mode in response to stable pulse oximetry measurements. In the embodiment shown, a data profile is provided that is indicative of the data received from a patient with a stable pulse and stable oxygen saturation. In an embodiment, it may not be desirable to operate the oximeter in high power mode while a patient is stable, healthy and in a non-critical situation.

The method 600 begins with a detection operation 602 that determines from the data that the oxygen saturation of the patient's blood has been within a predetermined range for a predetermined time interval. In response, a switching operation 604 is performed in which the pulse oximeter is switched to a low power mode corresponding to the stable patient data profile. The low power mode associated with a stable patient may be any one or more of the low power modes described above.

Furthermore, in the embodiment shown, the method 600 remains in the low power mode for another predetermined time interval and, after the time interval has elapsed, returns the pulse oximeter to the high power mode in high power mode operation 606.

Figure 7:
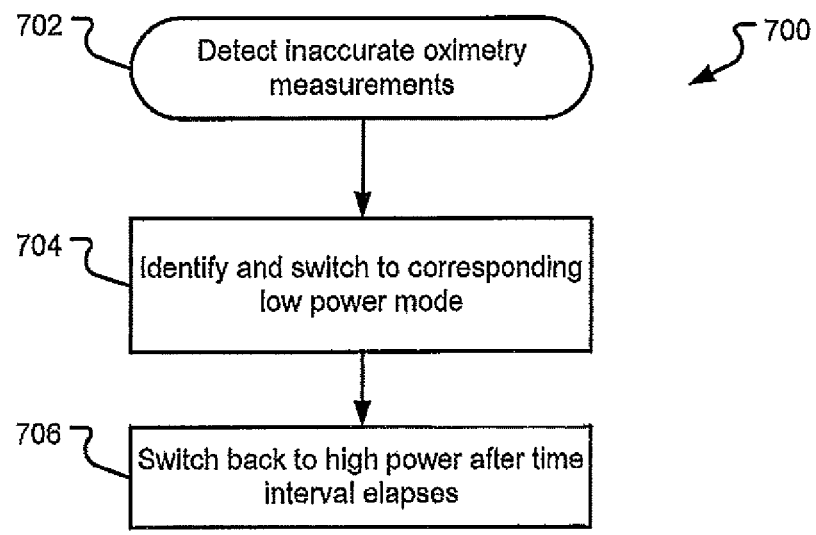
FIG. 7 illustrates an embodiment of a method for selecting a low power mode in response to detection of poor oximetry measurements.

FIG. 7 illustrates an embodiment of a method for selecting a low power mode in response to detection of poor oximetry measurements. In the embodiment shown, a data profile is provided that is indicative of a pulse oximeter that is not properly installed on a patient or that is otherwise not obtaining an accurate oxygen saturation measurement. In an embodiment, this may result in both an alarm and in the switching of the oximeter into a low power mode in order to conserve battery power.

The method 700 begins with a detection operation 702 that determines from the data that the pulse oximeter is not obtaining accurate oxygen saturation measurements of the patient's blood for a predetermined time interval. For example, the pulse oximeter may determine in the detection operation 7b02 that the sensor is not installed on the patient or that the sensor is not generating a signal. In response, a switching operation 704, which may include issuing an alarm, is performed in which the pulse oximeter is switched to a low power mode corresponding to the data profile. The low power mode associated with inaccurate readings may be a mode in which no measurements are taken or any one or more of the low power modes described above. The system may return to a high power mode upon detection of a change in data being generated or after the expiration of a predetermined time period, as shown in high power mode operation 706.

Figure 8:
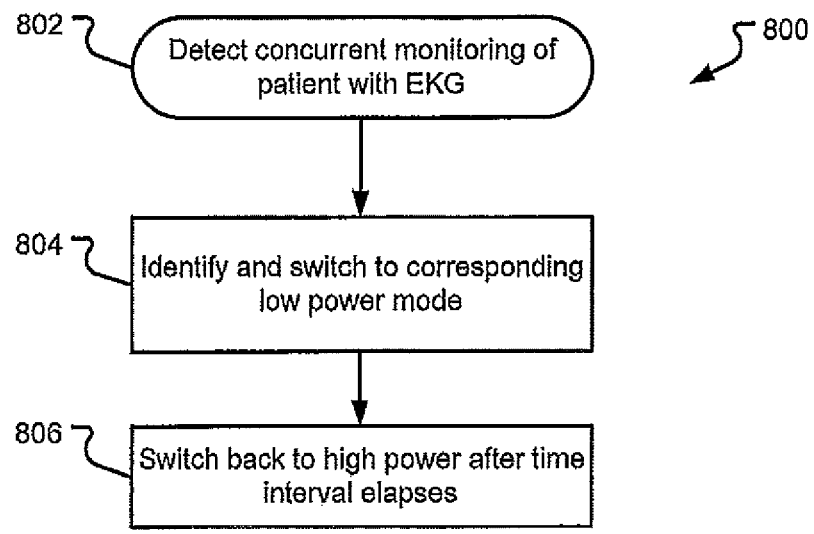
FIG. 8 illustrates an embodiment of a method for selecting a low power mode in response to detection that the patient is being monitored by an electrocardiograph (EKG) at the same time the pulse oximetry data is being taken.

FIG. 8 illustrates an embodiment of a method for selecting a low power mode in response to detection that the patient is being monitored by an electrocardiograph at the same time the pulse oximetry data is being taken. When a pulse oximeter is used in conjunction with an electrocardiograph, the caregivers have a second method of monitoring the heart function of a patient. Such a situation may be considered non-critical for pulse oximetry measurements because proper heart function can be determined directly from the electrocardiograph.

In the embodiment illustrated in FIG. 8, the method 800 includes a detection operation 802 that determines that the electrocardiograph is monitoring heart activity of the patient. This may be determined by detection of the data generated by the electrocardiograph to which the oximetry has access. In response, a switching operation 804 identifies a low power mode for use by the oximeter in conjunction with the electrocardiograph. The low power mode associated with a patient concurrently monitored by an electrocardiograph may be any one or more of the low power modes described above. The system may return to a high power mode upon detection of a change in data being generated or after the expiration of a predetermined time period, as shown by high power mode operation 806.

Figure 9:
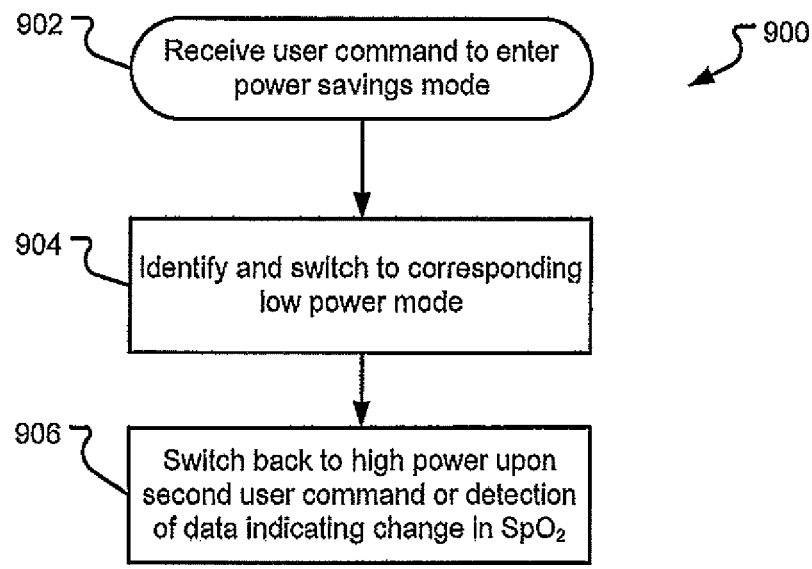
FIG. 9 illustrates an embodiment of a method for selecting a low power mode in response to a command received from an operator.

FIG. 9 illustrates an embodiment of a method for selecting a low power mode in response to a command received from an operator. In this method, an operator of the system can select a low power mode directly in order to conserve power. Such a selection may be considered detection of data that matches a data profile indicative of a non-critical situation and the system may enter a low power mode.

In the embodiment shown, the method 900 begins with a receive low power mode command 902. In response, a switching operation 904 identifies a low power mode for use by the oximeter when commanded into a power saving mode by a user. The low power mode associated with such a power saving state may be any one or more of the low power modes described above. The system may return to a high power mode upon detection of a change in data being generated, a second user command or after the expiration of a predetermined time period, as shown in high power mode operation 906.

It will be clear that the described systems and methods are well adapted to attain the ends and advantages mentioned as well as those inherent therein. Those skilled in the art will recognize that the methods and systems described within this specification may be implemented in many manners and as such is not to be limited by the foregoing exemplified embodiments and examples. In other words, functional elements being performed by a single or multiple components, in various combinations of hardware and software, and individual functions can be distributed among software applications and even different hardware platforms. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the described technology. Numerous other changes may be made which will readily suggest themselves to those skilled in the art and which are encompassed in the spirit of the invention disclosed and as defined in the appended claims.

What is claimed is:

1. A method for measuring oxygen saturation of a patient's blood comprising:
    operating a pulse oximeter in a high power mode, the pulse oximeter utilizing a sensor configured to generate data indicative of the oxygen saturation of the patient's blood;
    comparing, via a processor of the pulse oximeter, the data generated by the pulse oximeter to a plurality of predefined data profiles that includes a first data profile associated with a moving patient and a second data profile associated with an improperly positioned pulse oximeter on the patient;
    detecting, via the processor, that the data matches the first data profile or the second data profile;
    selecting, via the processor, a low power mode from a plurality of different low power modes that consume comparatively less power than the high power mode, wherein a first low power mode of the plurality of different low power modes is selected when the data matches the first data profile and a second low power mode of the plurality of different low power modes that is different from the first low power mode is selected when the data matches the second data profile;
    switching, via the processor, the pulse oximeter from the high power mode to the selected first low power mode or second low power mode for a first time interval;
    monitoring, via the processor, the oxygen saturation of the patient's blood while the pulse oximeter is in the selected first low power mode or second low power mode; and
    after the first time interval, returning, via the processor, the pulse oximeter to the high power mode.

2. The method of claim 1, wherein detecting that the data matches the first data profile or the second data profile comprises determining from the data that patient movement or an improperly positioned pulse oximeter, respectively, is affecting the characteristics of the data generated by the pulse oximeter in the high power mode.

3. The method of claim 1, wherein a third data profile is associated with a patient with a stable pulse and stable oxygen saturation and determining comprises:
    determining from the data that the oxygen saturation of the patient's blood has been within a predetermined range for a time interval; and
    identifying the data as matching the second data profile.

4. The method of claim 1, wherein determining comprises:
    determining, based at least in part upon the data, that the sensor is not installed on the patient.

5. The method of claim 1, wherein each of the plurality of predefined data profiles is associated with a different low power mode of the plurality of different low power modes and selecting comprises:
    identifying the low power mode of the plurality of different low power modes associated with the at least one predefined data profile matching the data.

6. The method of claim 1, wherein the plurality of predefined data profiles comprises
    a third data profile associated with a pulse oximeter that is used in conjunction with an electrocardiograph monitoring the patient.

7. The method of claim 1, wherein:
the first low power mode comprises reducing a number of samples taken within a period of time, reducing a signal-to-noise ratio of data generated by the pulse oximeter, using a different data processing algorithm than that used in the high power mode, causing the pulse oximeter to obtain data from only one of a plurality of light sources in the sensor, and reducing a sampling resolution of the data generated by the pulse oximeter; and the second low power mode comprises at least one of reducing a number of samples taken within a period of time, reducing a signal-to-noise ratio of data generated by the pulse oximeter, using a different data processing algorithm than that used in the high power mode, causing the pulse oximeter to obtain data from only one of a plurality of light sources in the sensor, and reducing a sampling resolution of the data generated by the pulse oximeter that is different from the first low power mode.

8. A pulse oximeter for determining oxygen saturation in a patient's blood comprising:
a high power mode of operation; and
a power conservation engine comprising a memory and a processor configured to execute instructions stored on the memory to compare data generated by the pulse oximeter to a plurality of data profiles and based at least in part upon determination that the data generated by the pulse oximeter matches at least one of the plurality of data profiles, to switch the pulse oximeter into one of a plurality of different low power modes of operation based at least in part upon the data profile matching the data generated by the pulse oximeter, wherein the plurality of data profiles comprises a first data profile associated with a moving patient and a second data profile associated with an improperly positioned pulse oximeter, wherein the power conservation engine switches the pulse oximeter to a first low power mode of the plurality of low power modes when the data profile matches the first data profile and switches the pulse oximeter to a second low power mode of the plurality of low power modes different from the first low power mode when the data profile matches the second data profile, and wherein the pulse oximeter monitors and records additional data while in the at least one of the plurality of different low power modes.

9. The pulse oximeter of claim 8, wherein the plurality of data profiles comprises a third data profile associated with a patient with a stable pulse and stable oxygen saturation.

10. The pulse oximeter of claim 8, wherein the plurality of data profiles comprises a fourth data profile associated with a pulse oximeter that is used in conjunction with an electrocardiograph monitoring the patient.

11. The pulse oximeter of claim 8, wherein the first or second low power reduce a number of oxygen saturation samples taken within a period of time in comparison with the high power mode.

12. The pulse oximeter of claim 8, wherein the first or the second low power mode reduces a signal-to-noise ratio of oxygen saturation data generated by the pulse oximeter.

13. The pulse oximeter of claim 8, wherein the first or the second low power mode uses a different data processing algorithm to determine oxygen saturation from the data than that used in the high power mode.

14. The pulse oximeter of claim 8, wherein the first or the second low power mode causes the pulse oximeter to use data from only one of a plurality of light sources in the pulse oximeter.

15. The pulse oximeter of claim 14, wherein the first or the second low power mode causes the pulse oximeter to generate data from one of a plurality of light sources in the pulse oximeter.

16. The pulse oximeter of claim 8, wherein the first or the second low power mode reduces a sampling resolution of the oxygen saturation data generated by the pulse oximeter.

17. The pulse oximeter of claim 8, wherein the power conservation engine is configured to receive a command from a user and to select one of the plurality of different low power modes based at least in part on the command from the user.

18. A pulse oximeter comprising:
a power conservation engine comprising a memory and a processor configured to execute instructions stored on the memory to:
compare data generated by the pulse oximeter to a plurality of data profiles, wherein each of the plurality of data profiles is associated with one of a plurality of different low power modes; and
based at least in part upon determination that the data generated by the pulse oximeter matches at least one of the plurality of data profiles, switch the pulse oximeter from a high power mode of operation into the low power mode of operation associated with the data profile matching the data generated by the pulse oximeter, wherein the plurality of data profiles comprises a first data profile associated with a moving patient and a second data profile associated with an improperly positioned pulse oximeter on the patient, wherein the power conservation engine switches the pulse oximeter to a first low power mode when the data matches the first data profile and switches the pulse oximeter into a second low power mode that is different from the first low power mode when the data matches the second data profile, and wherein the pulse oximeter monitors and records additional data while in the low power mode of operation.

* * * * *